United States Patent
Venugopala et al.

(10) Patent No.: US 12,227,516 B1
(45) Date of Patent: *Feb. 18, 2025

(54) SELECTIVE COX-2 INHIBITION OF 2-(SUBSTITUTED BENZYL)-3,5,6,7-TETRAHYDRO-4H-CYCLOPENTA[4,5]THIENO[2,3-D]PYRIMIDIN-4-ONES AND 4-FLUORO-N-(4-OXO-3,5,6,7-TETRAHYDRO-4H-CYCLOPENTA[4,5]THIENO[2,3-D]PYRIMIDIN-2-YL)BENZAMIDE AS ANTI-INFLAMMATORY AGENTS

(71) Applicant: KING FAISAL UNIVERSITY, Al-Ahsa (SA)

(72) Inventors: Katharigatta N. Venugopala, Al-Ahsa (SA); Pran Kishore Deb, Ranchi (IN); Raghu Prasad Mailavaram, Dhule (IN); Nizar A. Al-Shar'i, Irbid (JO); Swastika Ganguly, Ranchi (IN); Bapi Gorain, Ranchi (IN); Annie Lee Pei Wen, Kuala Lumpur (MY); Goh Hui Shan, Kuala Lumpur (MY)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/371,095

(22) Filed: Sep. 21, 2023

(51) Int. Cl.
 *C07D 495/04* (2006.01)
(52) U.S. Cl.
 CPC .................................. *C07D 495/04* (2013.01)
(58) Field of Classification Search
 CPC .................................................. C07D 495/04
 See application file for complete search history.

(56) References Cited

FOREIGN PATENT DOCUMENTS

CN 106905347 A * 6/2017 .......... C07D 495/04
WO 2016133888 A1 8/2016

OTHER PUBLICATIONS

Argoff (Year: 2000).*
CASRN1225504-78-8 (Year: 2010).*
Ouyang (Year: 2017).*
CN106905347A, Machine Translation (Year: 2017).*
Sirisha (Year: 2010).*
PubChem CID 28868365 (Year: 2009).*
Deb et al (Year: 2018).*
Pubchem, 10-(4-Fluorophenyl)-7-Thia-9,11 Diazatricyclo[6.4.0.02,6]Dodeca-1(8),2(6),9-Trien-12-One (Nov. 26, 2010).
Pubchem, 10-[(4-Methoxyphenyl)Methyl]-7-Thia-9,11-Diazatricyclo[6.4.0.02,6]Dodeca-1(8),2(6), 9-Trien-12-One (May 28, 2009).
Pubchem, 2-(4-methoxyphenyl)-3,5,6,7-tetrahydro-4Hcyclopenta[4,5]thieno[2,3-d]pyrimidin-4-one (Oct. 26, 2006).
Wang et al., "Inhibition of Tumor Cell Proliferation by Thieno[2,3-D]Pyrimidin-4(1H)-One-Based Analogs", Bioorganic & Medicinal Chemistry Letters, vol. 15, Issue 16, Aug. 15, 2005, pp. 3763-3766.
Pubchem, 10-[(4-Fluorophenyl)Methyl]-11-Prop-2-Ynyl-7-Thia-9,11-Diazatricyclo[6.4.0.02,6] Dodeca-1(8),2(6),9-Trien-12-One (Jul. 6, 2010).

* cited by examiner

*Primary Examiner* — Jeffrey S Lundgren
*Assistant Examiner* — Ibrahim D Bori
(74) *Attorney, Agent, or Firm* — Nath, Goldberg & Meyer; Joshua B. Goldberg

(57) ABSTRACT

Novel 2-(substituted benzyl)-3,5,6,7-tetrahydro-4H-cyclopenta[4,5]thieno[2,3-d]pyrimidin-4-ones and 4-fluoro-N-(4-oxo-3,5,6,7-tetrahydro-4H-cyclopenta[4,5]thieno[2,3-d]pyrimidin-2-yl)benzamide compounds, a method of synthesizing said compounds, a pharmaceutical composition comprising said compounds and a suitable carrier, and a method of using the compounds. The 2-(substituted benzyl)-3,5,6,7-tetrahydro-4H-cyclopenta[4,5]thieno[2,3-d]pyrimidin-4-ones and 4-fluoro-N-(4-oxo-3,5,6,7-tetrahydro-4H-cyclopenta[4,5]thieno[2,3-d]pyrimidin-2-yl)benzamide compounds, identified as COX-2 inhibitors, are useful as anti-inflammatory and pain agents.

4 Claims, No Drawings

SELECTIVE COX-2 INHIBITION OF 2-(SUBSTITUTED BENZYL)-3,5,6,7-TETRAHYDRO-4H-CYCLOPENTA[4,5]THIENO[2,3-D] PYRIMIDIN-4-ONES AND 4-FLUORO-N-(4-OXO-3,5,6,7-TETRAHYDRO-4H-CYCLOPENTA[4,5]THIENO[2,3-D] PYRIMIDIN-2-YL)BENZAMIDE AS ANTI-INFLAMMATORY AGENTS

BACKGROUND

1. Field

The present disclosure provides novel 2-(substituted benzyl)-3,5,6,7-tetrahydro-4H-cyclopenta[4,5]thieno[2,3-d]pyrimidin-4-ones derivatives and 4-fluoro-N-(4-oxo-3,5,6,7-tetrahydro-4H-cyclopenta[4,5]thieno[2,3-d]pyrimidin-2-yl) benzamide compounds that inhibit COX-2, an enzyme responsible for inflammation and pain, compositions containing such compounds and method of preparation. These compounds and compositions are useful as therapeutic agents for reducing pain and inflammation.

2. Description of the Related Art

Non-steroidal anti-inflammatory drugs (NSAIDs) have been therapeutically used in the medication of rheumatic arthritis and also in the treatment of various inflammatory disorders. Due to its gastrointestinal side effects, these are used in limited numbers.

Thus, there exists a need to develop anti-inflammatory agents which may not cause gastrointestinal side effects.

SUMMARY

The present subject matter relates to the use of novel 2-(substituted benzyl)-3,5,6,7-tetrahydro-4H-cyclopenta[4,5]thieno[2,3-d]pyrimidin-4-ones and 4-fluoro-N-(4-oxo-3,5,6,7-tetrahydro-4H-cyclopenta[4,5]thieno[2,3-d]pyrimidin-2-yl)benzamide derivatives as anti-inflammatory agents to be used in the place of NSAIDs which are known to cause gastrointestinal problems.

In this regard, the present subject matter relates to a series of 2-(substituted benzyl)-3,5,6,7-tetrahydro-4H-cyclopenta[4,5]thieno[2,3-d]pyrimidin-4-ones and 4-fluoro-N-(4-oxo-3,5,6,7-tetrahydro-4H-cyclopenta[4,5]thieno[2,3-d]pyrimidin-2-yl)benzamide as anti-inflammatory agents. In an effort to develop novel anti-inflammatory agents, a series of 2-(substituted benzyl)-3,5,6,7-tetrahydro-4H-cyclopenta[4,5]thieno[2,3-d]pyrimidin-4-ones and 4-fluoro-N-(4-oxo-3,5,6,7-tetrahydro-4H-cyclopenta[4,5]thieno[2,3-d]pyrimidin-2-yl)benzamide have been achieved by a synthetic chemical method and purified by recrystallization and column chromatographic methods. Structural elucidation of the compounds is completed by spectral techniques such as FT-IR, NMR ($^1$H and $^{13}$C), LC-MS, and elemental analysis. These compounds were evaluated for their anti-inflammatory activity and some show promising anti-inflammatory activity between millimolar to micromolar concentrations compared to standard anti-inflammatory drugs. Some of the selected lead compounds can be successfully taken forward to develop novel anti-inflammatory drug candidates.

Accordingly, the present subject matter relates the use of novel 2-(substituted benzyl)-3,5,6,7-tetrahydro-4H-cyclopenta[4,5]thieno[2,3-d]pyrimidin-4-ones and 4-fluoro-N-(4-oxo-3,5,6,7-tetrahydro-4H-cyclopenta[4,5]thieno[2,3-d]pyrimidin-2-yl)benzamide derivatives for inhibiting COX-1 and COX-2 isoenzymes which are known to cause inflammation in the body. Reducing inflammation can decrease pain, swelling, and illnesses and diseases associated with excess inflammation. The present subject matter further provides a process for the synthesis of such compounds, pharmaceutical compositions containing these compounds, and their use in therapy for the treatment of inflammation in a patient, either alone or in combination with other active ingredients.

In an embodiment, the present subject matter relates to a compound having the formula I:

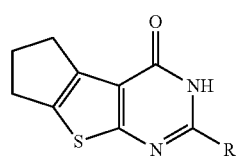

or a pharmaceutically acceptable salt, ester, stereoisomer, or solvate thereof, wherein:

R is selected from the group consisting of -phenyl, —CH$_2$phenyl, and —NHCOphenyl, wherein each phenyl is substituted with one or more substituents selected from the group consisting of halogen and methoxy.

In another embodiment, the present subject matter relates to a compound having the formula I:

or a pharmaceutically acceptable salt, ester, stereoisomer, or solvate thereof, wherein:

R is selected from the group consisting of -phenyl, —CH$_2$phenyl, and —NHCOphenyl, wherein each phenyl is substituted with one or more substituents selected from the group consisting of fluorine and methoxy.

In an embodiment, the present subject matter relates to a compound selected from the group consisting of: 2-(4-Fluorobenzyl)-3,5,6,7-tetrahydro-4H-cyclopenta[4,5]thieno[2,3-d]pyrimidin-4-one (6), 2-(4-Methoxybenzyl)-3,5,6,7-tetrahydro-4H-cyclopenta[4,5]thieno[2,3-d]pyrimidin-4-one (7), 2-(4-Methoxyphenyl)-3,5,6,7-tetrahydro-4H-cyclopenta[4,5]thieno[2,3-d]pyrimidin-4-one (8), 4-Fluoro-N-(4-oxo-3,5,6,7-tetrahydro-4H-cyclopenta[4,5]thieno[2,3-d]pyrimidin-2-yl)benzamide (9), and a pharmaceutically acceptable salt, ester, stereoisomer, or solvate thereof.

In an embodiment, the present subject matter relates to a process for the synthesis of the compounds of formula I, including a number of species or specific structures falling under structural formula I. Further contemplated herein are pharmaceutical compositions containing these compounds, as well as methods of inhibiting COX-1 and COX-2 isoenzyme activity and of treating inflammation by administering the present compounds to a patient in need thereof.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, and bromo.

As used herein, "heteroatom" refers to an atom of any element other than carbon or hydrogen and includes, for example, nitrogen, oxygen, silicon, sulfur, phosphorus, and selenium.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as inflammation.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a compound having the formula I:

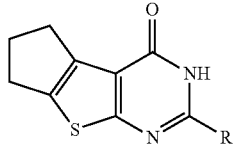

or a pharmaceutically acceptable salt, ester, stereoisomer, or solvate thereof, wherein:

R is selected from the group consisting of -phenyl, —CH$_2$phenyl, and —NHCOphenyl, wherein each phenyl is substituted with one or more substituents selected from the group consisting of halogen or methoxy.

In yet another embodiment, the present subject matter relates to compounds of formula I, wherein R is—CH$_2$phenyl substituted with a fluorine. In an embodiment in this regard, the compound can have a melting point between 284° C. and 286° C.

In one embodiment, the present subject matter relates to a compound of formula I, wherein R is—CH$_2$phenyl substituted with a methoxy group. In an embodiment in this regard, the compound can have a melting point between 276° C. and 280° C.

In a further embodiment, the present subject matter relates to a compound of formula I, wherein R is a -phenyl group substituted with a methoxy group. In an embodiment in this regard, the compound can have a melting point greater than 300° C.

In a further embodiment, the present subject matter relates to a compound of formula I, wherein R is a—NHCOPhenyl substituted with a fluorine. In an embodiment in this regard, the compound can have a melting point greater than 300° C.

In another embodiment, the present subject matter relates to a compound having the formula I:

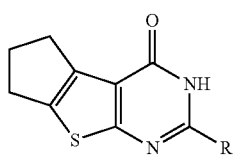

or a pharmaceutically acceptable salt, ester, stereoisomer, or solvate thereof, wherein:

R is selected from the group consisting of -phenyl, —CH$_2$phenyl, and —NHCOphenyl, wherein each phenyl is substituted with one or more substituents selected from the group consisting of fluorine or methoxy.

In an embodiment, the present subject matter relates to a compound selected from the group consisting of: 2-(4-Fluorobenzyl)-3,5,6,7-tetrahydro-4H-cyclopenta[4,5]thieno[2,3-d]pyrimidin-4-one (6), 2-(4-Methoxybenzyl)-3,5,6,7-tetrahydro-4H-cyclopenta[4,5]thieno[2,3-d]pyrimidin-4-one (7), 2-(4-Methoxyphenyl)-3,5,6,7-tetrahydro-4H-cyclopenta[4,5]thieno[2,3-d]pyrimidin-4-one (8), 4-Fluoro-N-(4-oxo-3,5,6,7-tetrahydro-4H-cyclopenta[4,5]thieno[2,3-d]pyrimidin-2-yl)benzamide (9), and a pharmaceutically acceptable salt, ester, stereoisomer, or solvate thereof.

Said differently, the present subject matter can relate to compounds of formula I selected from the group consisting of:

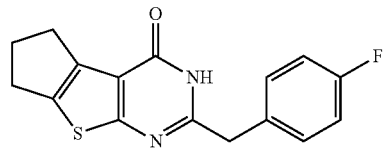 [SMILES: O=c1[nH]c(Cc2ccc(F)cc2)nc2sc3c(c12)CCC3]

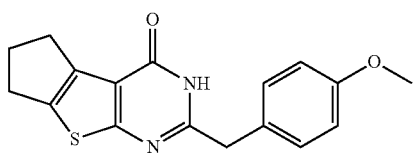 [SMILES: COc1ccc(Cc2nc3sc4c(c3c(=O)[nH]2)CCC4)cc1]

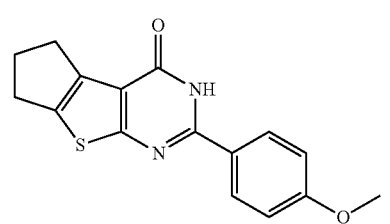

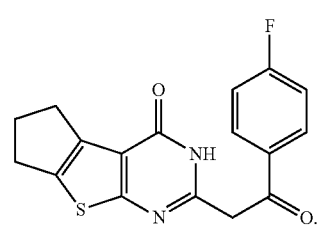

and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to the following general synthetic pathway.

Specifically, synthesis commences with mixing cyclopentanone, sulphur in ethanol, and ethylcyanoacetate in a conical flask and stirring at room temperature. Then diethylamine is added dropwise with constant stirring for at least about 1 hour. A constant temperature of at least about 45° C. is applied. The product is filtered, dried and purified by recrystallisation from ethanol to get the compound ethyl-2-amino-4,5,6-trihydrobenzo[b]thiophene-3-carboxylate (4) as outlined in Scheme 1.

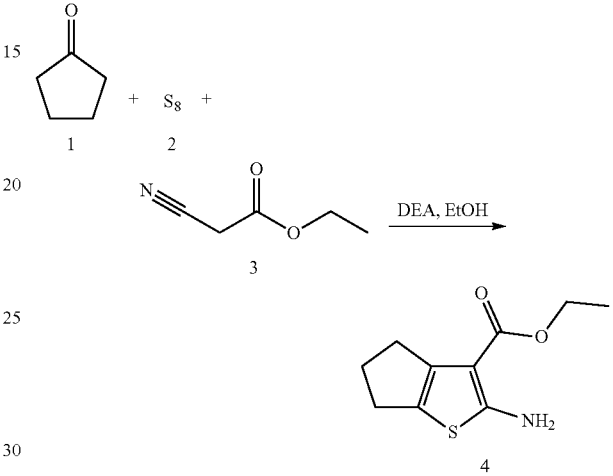

To a solution of ethyl-2-amino-4,5,6-trihydrobenzo[b]thiophene-3-carboxylate (4), cyanamide and concentrated HCl solution are added into a round bottom flask and refluxed for at least about 6 hours at between 50° C. and 60° C., or at about 55° C. Then the reaction mixture is neutralized with diluted NaOH. The precipitate formed is filtered, dried, and re-crystallized with ethanol to obtain pure 2-amino-5,6,7-trihydrobenzo[b]thieno[2,3-d]pyrimidin-4(3H)-one (5) as outlined in Scheme 2.

Scheme 2

A mixture of ethyl-2-amino-4,5,6-trihydrobenzo[b]thiophene-3-carboxylate (4) and 4-fluorophenylacetonitrile are weighed and taken in a conical flask. The mixture is dissolved in 1,4-dioxane and a stream of dry hydrogen chloride gas is passed through the mixture for at least about 2 days. After at least about 2 days, the mixture is poured into a beaker and neutralized with diluted sodium hydroxide. The resultant precipitate formed is filtered, dried, and recrystallized by using ethanol to yield the pure product 2-(4-fluorobenzyl)-5,6,7-trihydrocyclopentathieno[2,3-d]pyrimidine-4(3H)-one (6) as outlined in Scheme 3.

Scheme 3

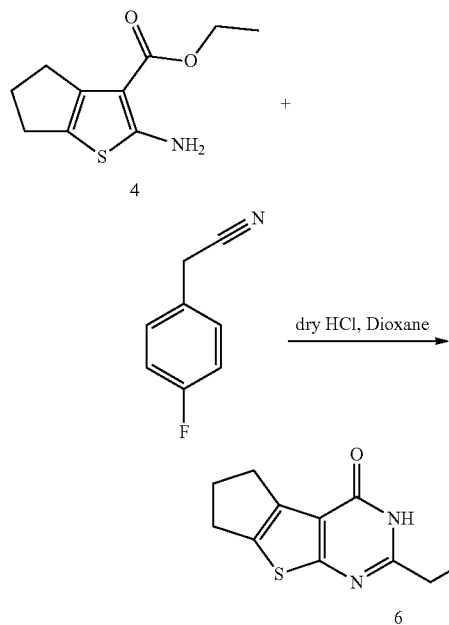

A mixture of ethyl-2-amino-4,5,6-trihydrobenzo[b]thiophene-3-carboxylate (4) and 4-methoxyphenylacetonitrile are weighed and taken in a conical flask. The mixture is dissolved in dioxane and a stream of dry hydrogen chloride gas is passed through the mixture for at least about 2 days. After at least about 2 days, the mixture is poured into a beaker and neutralized with diluted sodium hydroxide. The resultant precipitate formed is filtered, dried, and recrystallized using ethanol to yield the pure product 2-(4-methoxybenzyl)-5,6,7-trihydrocyclopentathieno[2,3-d]pyrimidine-4(3H)-one (7) as outlined in Scheme 4.

Scheme 4

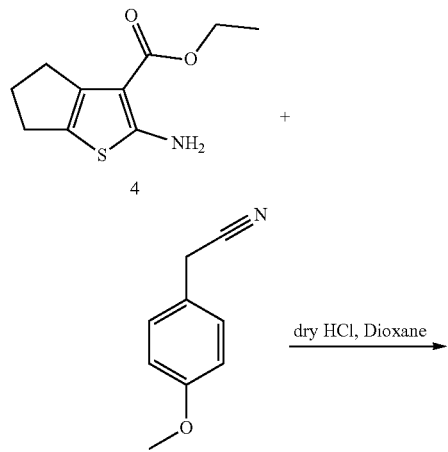

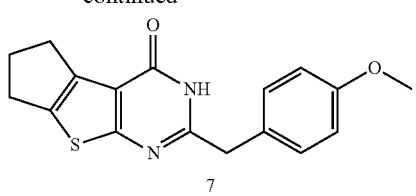

A mixture of ethyl-2-amino-4,5,6-trihydrobenzo[b]thiophene-3-carboxylate (4) and 4-methoxybenzonitrile is dissolved in 1,4-dioxane in a conical flask. Dry hydrogen chloride gas is passed through the mixture for at least 48 hours. The reaction mixture is then neutralized with 10% sodium hydroxide. The resultant precipitate is purified by recrystallization to get pure compound 2-(4-methoxyphenyl)-3,5,6,7-tetrahydro-4H-cyclopenta[4,5]thieno[2,3-d]pyrimidin-4-one (8) as outlined in Scheme 5.

Scheme 5

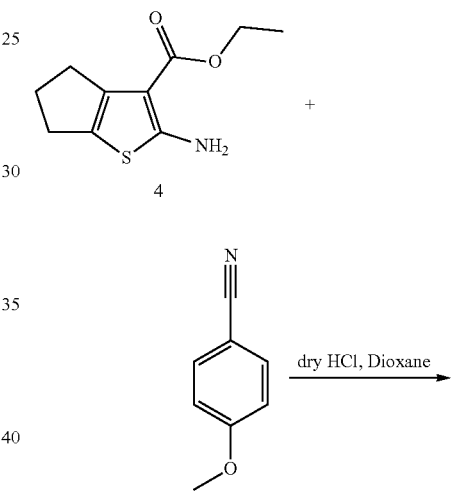

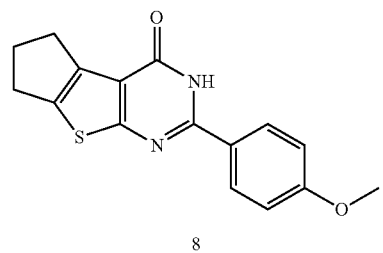

Synthesizing the final compound involves dissolving 2-amino-5,6,7-trihydrobenzo[b]thieno[2,3-d]pyrimidin-4(3H)-one (5) in dimethylformamide. Then sodium hydride is added to the mixture with constant stirring for at least about 1 hour at between about 0° C. to about 5° C. It is followed by dropwise addition of 4-fluorobenzoyl chloride. After about 24 hours, the reaction mixture is neutralized and proceeded to extraction with ethylacetate. The upper organic layer is collected and dried with anhydrous sodium sulphate and the residue is purified to yield the compound 4-fluoro-N-(4-oxo-3,5,6,7-tetrahydro-4H-cyclopenta[4,5]thieno[2,3-d]pyrimidin-2-yl)benzamide 9 as outline in Scheme 6.

Scheme 6

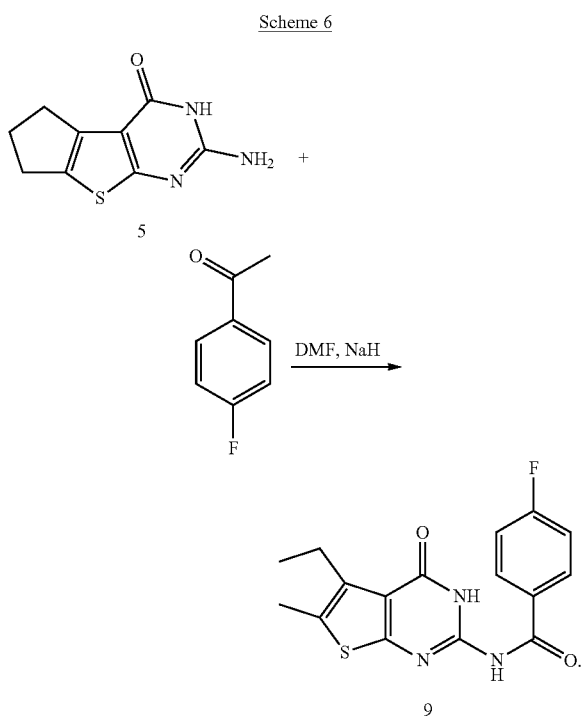

In another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one or two of the present compounds, or one of the present compounds.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for inflammation. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of inflammation, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid, or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol, or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. Accordingly, the present subject matter further relates to use of the present compounds for the treatment of inflammation and diseases associated with inflammation. Similarly, the present compounds can be used to inhibit COX-1 and COX-2 enzyme activity in a patient. The present compounds may also be used to treat pain and swelling associated with inflammation.

Accordingly, in an embodiment of the present subject matter, the 2-(substituted benzyl)-3,5,6,7-tetrahydro-4H-cyclopenta[4,5]thieno[2,3-d]pyrimidin-4-ones derivatives and 4-fluoro-N-(4-oxo-3,5,6,7-tetrahydro-4H-cyclopenta[4,5]thieno[2,3-d]pyrimidin-2-yl)benzamide derivatives, or the 2-(substituted benzyl)-3,5,6,7-tetrahydro-4H-cyclopenta[4,5]thieno[2,3-d]pyrimidin-4-ones derivatives and 4-fluoro-N-(4-oxo-3,5,6,7-tetrahydro-4H-cyclopenta[4,5]thieno[2,3-d]pyrimidin-2-yl)benzamide derivatives, as described herein engaged for in vitro study towards the ovine COX-1 and human recombinant COX-2 isoenzymes can display a mild selective inhibition against COX-2. The inhibitory activity of the tested compounds was determined based on $IC_{50}$ values, whereas the selectivity was based on their selectivity indices (SI), which are defined as COX-1 $IC_{50}$/COX-2 $IC_{50}$.

In another embodiment, a present compound (6) engaged for in vitro study can display a COX-1 $IC_{50}$ concentration of 38.52 μM, COX-2 $IC_{50}$ concentration of 56.40 μM and an SI of 0.68, at an incubation time of at least 18 hrs.

In a further embodiment, a present compound (7) engaged for in vitro study can display a COX-1 $IC_{50}$ concentration of 223.74 μM, COX-2 $IC_{50}$ concentration of 32.06 μM and an SI of 6.98 at an incubation time of at least 18 hrs.

In an embodiment, a present compound (8) engaged for in vitro study can display a COX-1 $IC_{50}$ concentration of 83.8 μM, COX-2 $IC_{50}$ concentration of 7.3 μM and an SI of 11.41 at an incubation time of at least 18 hrs.

In another embodiment, a present compound (9) engaged for in vitro study can display a COX-1 $IC_{50}$ concentration of 69.2 μM, COX-2 $IC_{50}$ concentration of 54.9 μM and an SI of 1.26 at an incubation time of at least 18 hrs.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used. Similarly, one or more of the present compounds can be used in combination therapy with one or more additional active agents.

The following examples relate to various methods of manufacturing certain specific compounds as described herein. All compound numbers expressed herein are with reference to the synthetic pathway figures shown above.

EXAMPLES

Example 1

Preparation of ethyl-2-amino-4,5,6-trihydrobenzo[b]thiophene-3-carboxylate (4)

Cyclopentanone (0.04 mol; 3.55 mL), sulphur (0.04 mol, 1.28 g) in ethanol (20 mL) and ethylcyanoacetate (0.04 mol; 4.26 mL) were mixed in a conical flask and stirred at room temperature. Diethylamine (0.04 mol, 4.20 mL) was then added dropwise with constant stirring over a 1-hour duration. Constant temperature of 45° C. was applied. The product was filtered, dried and purified by recrystallisation from ethanol to get ethyl-2-amino-4,5,6-trihydrobenzo[b]thiophene-3-carboxylate 4.

Elemental Analysis: Yield: 72%. Brown powder, mp. 86-90, Rf (Hexane:EtAc (6:4))=0.9, FT-IR (KBR, cm$^{-1}$): 3400, 3296 (NH$_2$), 2982, 2928, 2903 (Aliphatic C—H), 1645 (C=O conj.), 1595, 1480 (Aromatic C=C), 1275 (C—O). $^1$H NMR (DMSO-d6) δ ppm: 5.88 (s, 2H, 2-NH$_2$), 4.25-4.21 (q, 2H, 3-COOCH$_2$CH$_3$), 2.81-2.79 (t, 2H, 6-CH$_2$), 2.70-2.69 (t, 2H, 4-CH$_2$), 2.31-2.28 (quin, 21-, 5-CH$_2$), 1.33-1.30 (t, 3H, 3-COOCH$_2$CH$_3$).

Example 2

Preparation of 2-amino-5,6,7-trihydrobenzo[b]thieno[2,3-d]pyrimidin-4(3H)-one (5)

First ethyl-2-amino-4,5,6-trihydrobenzo[b]thiophene-3-carboxylate 4 (0.01 mol, 2 g), cyanamide (2 g), and concentrated HCl solution (2 mL) were added into a round bottom flask and refluxed for 6 hours at 55° C. Then, the reaction mixture was neutralized with diluted NaOH (10%) solution. The precipitate formed was filtered, dried, and re-crystalized with ethanol to obtain a pure compound of 2-amino-5,6,7-trihydrobenzo[b]thieno[2,3-d]pyrimidin-4(3H)-one (5).

Elemental Analysis: Yield: 80%. Light brown powder, mp.>300, Rf (Hexane:EtAc (6:4)) 0.2, FT-IR (KBR, cm$^{-1}$): 3399, 3296 (NH$_2$); 2982, 2928, 2903 (Aromatic C—H); 1645 (C=O); 1595, 1499 (Aromatic C=C). $^1$H NMR (DMSO-d$_6$) δ ppm: 10.82 (s, 1H, 3-NH); 6.41 (s, 2H, 2-NH$_2$); 2.78-2.74 (m, 4H, 5-CH$_2$ and 7-CH$_2$), 2.29-2.25 (m, 2H, 6-CH$_2$).

Example 3

Preparation of 2-(4-fluorobenzyl)-5,6,7-trihydrocyclopentathieno[2,3-d]pyrimidine-4(3H)-one First ethyl-2-amino-4,5,6-trihydrobenzo[b]thiophene-3-carboxylate (4) (0.01 mol; 2.23 g) and 4-fluorophenylacetonitrile (0.015 mol; 2.03 g) were weighed and taken in a conical flask. The mixture was then dissolved in 1,4-dioxane (10 mL) and a stream of dry hydrogen chloride gas was passed through the mixture for 2 days. After 2 days, the mixture was poured into a beaker and neutralized with diluted sodium hydroxide (10%). The resultant precipitate formed was filtered, dried, and recrystallized by using ethanol to yield the pure product 2-(4-fluorobenzyl)-5,6,7-trihydrocyclopentathieno[2,3-d]pyrimidine-4(3H)-one (6).

Elemental Analysis: Yield: 25%. Light yellowish-brown powder, mp. 284-286° C., Rf (Hexane:EtAc, 6:4)=0.9, FT-IR (KBR, cm$^{-1}$): 813.96 (Para disubstituted ring), 1222.87 (C—F), 1479.40 (Methylene Groups), 1587.42 (N—H bending), 1662.64 (Amide C=O), 393.82 (Aromatic C—H), 3305.99 (Secondary amides). $^1$H NMR (DMSO-d$_6$) δ ppm: 12.5 (s, 1H, 3-NH), 7.364-7.336 (m, 2H, Ar—H), 7.139-7.104 (m, 2H, Ar—H), 3.893 (s, 2H, 2-CH$_2$), 2.850-20847 (m, 4H, 5-CH$_2$, 6-CH$_2$), 2.361-2.331 (m, 2H, 7CH$_2$). ESI-MS (m/z; %) 300 (M*+1; 100).

Example 4

Preparation of 2-(4-methoxybenzyl)-5,6,7-trihydrocyclopentathieno[2,3-d]pyrimidine-4(3H)-one (7)

First ethyl-2-amino-4,5,6-trihydrobenzo[b]thiophene-3-carboxylate (4) (0.01 mol; 2.23 g) and 4-methoxyphenylacetonitrile (6) (0.015 mol; 2.21 g) were weighed and taken in a conical flask. The mixture was then dissolved in dioxane (10 mL) and a stream of dry hydrogen chloride gas was passed through the mixture for 2 days. After 2 days, the mixture was poured into a beaker and neutralized with diluted sodium hydroxide (10%). The resultant precipitate formed was filtered, dried, and recrystallized using ethanol to yield the pure product 2-(4-methoxybenzyl)-5,6,7-trihydrocyclopentathieno[2,3-d]pyrimidine-4(3H)-one (7).

Elemental Analysis: Yield: 30%. White powder, mp. 276-280° C., Rf (CHCl$_3$: Acetone, 9:1)=0.9, FT-IR (KBR, cm$^{-1}$): 813.96 (Para disubstituted ring), 1244.09 (Ether), 1357.89 (CH$_3$), 1456.26 (Methylene groups), 1587.42 (Aromatic C=C), 1660.71 (C=O Amide), 3005.10 (C—H stretch), 3304.06 (Secondary Amide). $^1$H NMR (CDCl$_3$) δ ppm: 12.460 (s, 1H, 3-NH), 7.243-7.226 (m, 2H, Ar—H), 6.864-6.846 (m, 2H, Ar—H), 3.810 (s, 1H, 2-CH$_2$), 3.723 (s, 3H, Ar—OCH$_3$), 2.863-2.836 (m, 4H, 5-CH$_3$, 6-CH$_3$), 2.362-2.304 (m, 2H, 7-CH$_2$). ESI-MS (m/z; %)=312 (M$^+$+1; 100).

Example 5

Preparation of 2-(4-methoxyphenyl)-3,5,6,7-tetrahydro-4H-cyclopenta[4,5]thieno[2,3-d]pyrimidin-4-one (8)

First ethyl-2-amino-4,5,6-trihydrobenzo[b]thiophene-3-carboxylate 4 (0.01 mol; 2.11 g) and 4-methoxybenzonitrile (0.015 mol; 2 g) were dissolved in 1,4-dioxane (10 mL) in a conical flask. Then dry hydrogen chloride gas was passed through the mixture for at least 48 hours. Next, the reaction mixture was then neutralized with 10% sodium hydroxide. The resultant precipitate was purified by recrystallization to get pure compound 8.

Elemental Analysis: Yield: 81%. White powder, mp.>300, Rf (Hexane:EtAc, 6:4)=0.4, FT-IR (KBR, cm$^{-1}$): 3173 (N—H), 3053 (Aromatic C—H), 2997, 2957, 2833 (Aliphatic C—H), 1661 (C=O), 1605 (C=N), 1524, 1478 (Aromatic C=C). $^1$H NMR (DMSO-d$_6$) δ ppm: 12.39 (s, 1H, 3-NH), 8.11-8.09 (m, 2H, Ar—H), 7.05-7.03 (m, 2H, Ar—H), 3.82 (s, 3H, 2-Ph-OCH$_3$), 2.93-2.88 (t, 4H, 5-CH$_2$ and 7-CH$_2$), 2.40-2.36 (quin, 2H, 6-CH$_2$). ESI-MS (m/z; %)=298.0 (M$^+$+1; 100).

Example 6

Preparation of 4-fluoro-N-(4-oxo-3,5,6,7-tetrahydro-4H-cyclopenta[4,5]thieno[2,3-d]pyrimidin-2-yl)benzamide (9)

First 2-amino-5,6,7-trihydrobenzo[b]thieno[2,3-d]pyrimidin-4(3H)-one (5) (0.002 mol; 0.42 g) was dissolved in dimethylformamide (5 mL). Then sodium hydride (0.016 mol; 0.38 g) was added to the mixture with constant stirring for 1 hour at 0-5° C. It was followed by dropwise addition of 4-fluorobenzoyl chloride (0.004 mol; 0.48 mL). After 24 hours, the reaction mixture was neutralized and proceeded to extraction with ethyl acetate. Lastly, the upper organic layer was collected and dried with anhydrous sodium sulphate and the residue was purified on a silica gel column using hexane:ethyl acetate (4:1) to yield 4-fluoro-N-(4-oxo-3,5,6,7-tetrahydro-4H-cyclopenta[4,5]thieno[2,3-d]pyrimidin-2-yl)benzamide (9).

Elemental Analysis: Yield: 20%. Yellow powder, mp.>300, Rf (Hexane:EtAc, 6:4)=0.8, FT-IR (KBR, cm$^{-1}$): 3298, 3228 (N—H), 3086 (Aromatic C—H), 2965, 2855 (Aliphatic C—H), 1678 (C=O), 1647 (C=N), 1585, 1548, 1494 (Aromatic C=C). $^1$H NMR (DMSO-d$_6$) δ ppm: 12.19 (s, 1H, 3-NH), 11.89 (s, 1H, 2-NH), 8.11 (m, 2H, Ar—H), 7.39-7.35 (m, 2H, Ar—H), 2.88-2.87 (t, 4H, 5-CH$_2$ and 7-CH$_2$), 2.38-2.36 (quin, 2H, 6-CH$_2$). ESI-MS (m/z; %)=329.0 (M$^+$+1; 100).

Pharmacological Activity

Example 7

In Vitro Cytotoxic Activity Assay

The COX (ovine) Inhibitor Screening Assay was performed mainly to determine the selective inhibition of tested compounds (6, 7, 8 and 9) towards the ovine COX-1 and human recombinant COX-2 isoenzymes. Adding arachidonic acid (AA) helped convert the COX component into PGG$_2$, followed by a reduction of PGG$_2$ into PGH$_2$. The following addition of SnCl$_2$ converted PGH$_2$ into PGF$_{2α}$. The assay directly measures the PGF$_{2α}$ via enzyme immunoassay (EIA) using a broadly specific antiserum that is bound to all PG tracers. Depending on the tested compounds inhibitory effect, the concentration of PGF$_{2α}$ in each well varied and was inversely proportional to the amount of PG tracers that were able to bind to the antiserum. PG tracers-antiserum complex was left to bind to the mouse monoclonal anti-rabbit antibody that had been coated to the well during the 18 hours of incubation. Ellman's reagent was added to give distinct yellow coloration to the products from this enzymatic reaction, which absorbed strongly at 412 nm. The intensity of the color was proportional to the amount of PG tracers-antiserum complex bound to the well, which was inversely proportional to the concentration of PGF$_{2α}$ present.

The inhibitory activity of tested compounds was determined based on IC$_{50}$ values, whereas the selectivity was based on their selectivity indices (SI), which are defined as COX-1 IC$_{50}$/COX-2 IC$_{50}$. In the assay system, indomethacin was used as a non-selective COX inhibitor standard, while NS-398 was used as a COX-2 selective inhibitor standard. The results revealed that both tested compounds (6, 7, 8 and 9) were showing mild selective inhibition against COX-2 as listed in Table 1.

TABLE 1

| | | Anti-inflammatory activity | | |
| --- | --- | --- | --- | --- |
| Compound code | Compound Structure | COX-1 IC$_{50}$ (μM) | COX-2 IC$_{50}$ (μM) | SI |
| 6 | (cyclopenta-thieno-pyrimidinone with 4-fluorobenzyl substituent) | 38.52 | 56.40 | 0.68 |
| 7 | (cyclopenta-thieno-pyrimidinone with 4-methoxybenzyl substituent) | 223.74 | 32.06 | 6.98 |

TABLE 1-continued

| Compound code | Compound Structure | Anti-inflammatory activity | | |
| --- | --- | --- | --- | --- |
| | | COX-1 IC$_{50}$ (µM) | COX-2 IC$_{50}$ (µM) | SI |
| 8 | 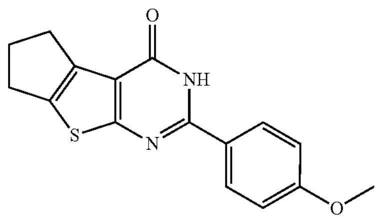 [SMILES: COc1ccc(-c2nc3sc4c(c3c(=O)[nH]2)CCC4)cc1] | 83.8 | 7.3 | 11.41 |
| 9 | 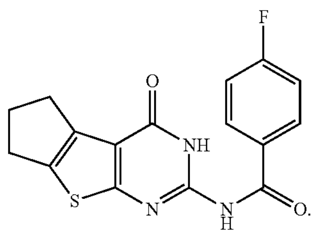 [SMILES: O=C(Nc1nc2sc3c(c2c(=O)[nH]1)CCC3)c1ccc(F)cc1] | 69.2 | 54.9 | 1.26 |

It is to be understood that the 2-(substituted benzyl)-3,5,6,7-tetrahydro-4H-cyclopental[4,5]thieno[2,3-d]pyrimidin-4-ones derivatives and 4-fluoro-N-(4-oxo-3,5,6,7-tetrahydro-4H-cyclopenta[4,5]thieno[2,3-d]pyrimidin-2-yl) benzamide derivatives are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A compound having the formula I:

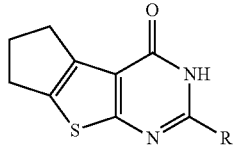

I or a pharmaceutically acceptable salt, ester, stereoisomer, or solvate thereof, wherein:

R is —NHCOPhenyl wherein the phenyl in the —NHCO-Phenyl is substituted with a fluorine.

2. A pharmaceutically acceptable composition comprising a therapeutically effective amount of the compound of claim 1 and a pharmaceutically acceptable carrier.

3. A compound that is:

4-Fluoro-N-(4-oxo-3,5,6,7-tetrahydro-4H-cyclopenta[4,5]thieno[2,3-d]pyrimidin-2-yl)benzamide (9), or a pharmaceutically acceptable salt, ester, stereoisomer, or solvate thereof.

4. A pharmaceutically acceptable composition comprising a therapeutically effective amount of the compound of claim 3 and a pharmaceutically acceptable carrier.

* * * * *